(12) United States Patent
Jain

(10) Patent No.: US 11,524,006 B2
(45) Date of Patent: Dec. 13, 2022

(54) CRENOLANIB FOR TREATING TRK KINASE ASSOCIATED PROLIFERATIVE DISORDERS

(71) Applicant: Arog Pharmaceuticals, Inc., Plano, TX (US)

(72) Inventor: Vinay K. Jain, Dallas, TX (US)

(73) Assignee: AROG PHARMACEUTICALS, INC., Plano, TX (US)

( * ) Notice: Subject to any disclaimer, the term of this patent is extended or adjusted under 35 U.S.C. 154(b) by 39 days.

(21) Appl. No.: 17/320,350

(22) Filed: May 14, 2021

(65) Prior Publication Data

US 2022/0079933 A1 Mar. 17, 2022

Related U.S. Application Data

(60) Provisional application No. 63/079,585, filed on Sep. 17, 2020.

(51) Int. Cl.
*A61K 31/4709* (2006.01)
*A61P 35/00* (2006.01)
*A61K 45/06* (2006.01)

(52) U.S. Cl.
CPC .......... *A61K 31/4709* (2013.01); *A61K 45/06* (2013.01)

(58) Field of Classification Search
CPC ............................ A61K 31/4709; A61P 35/00
USPC ......................................................... 514/394
See application file for complete search history.

(56) References Cited

U.S. PATENT DOCUMENTS

| | | | |
|---|---|---|---|
| 2,731,954 | A | 1/1956 | O'Shei |
| 5,990,146 | A | 11/1999 | Boschelli et al. |
| 7,183,414 | B2 | 2/2007 | Tom et al. |
| 2005/0124599 | A1 | 6/2005 | Kath et al. |
| 2018/0117031 | A1 | 5/2018 | Jain |
| 2019/0000840 | A1 | 1/2019 | Li et al. |

FOREIGN PATENT DOCUMENTS

| | | |
|---|---|---|
| WO | 1999016755 A1 | 4/1999 |
| WO | 2001040217 A1 | 6/2001 |
| WO | 2020114499 A1 | 6/2020 |

OTHER PUBLICATIONS

Eggert, et al. "Expression of the neurotrophin receptor TrkB is associated with unfavorable outcome in Wilms' tumor." J Clin Oncol 19(3): 689-696. (Feb. 2001).
U.S. Food and Drug Administration, (Vitrakvi® (larotrectinib) Label, capsules, for oral use Vitrakvi® (larotrectinib) oral solution—Initial U.S Approval: 2018.
U.S. Food and Drug Administration, Rozlytrek (entrectinib) Label, capsules, for oral use Initial U.S. Approval: 2019.
Goldberg, et al. "Younger Patients with Newly Diagnosed FLT3-Mutant AML Treated with Crenolanib Plus Chemotherapy Achieve Durable Remissions" Power Point Presentation, EHA. (2020).
Hyman, et al. "Abstract CT127: Phase I and expanded access experience of LOXO-195 (Bay 2731954), a selective next-generation TRK inhibitor (TRKi)." Cancer Research 79(13 Supplement): CT127-CT127. (2019). Abstract Only.
Marchetti, et al. "Frequent mutations in the neurotrophic tyrosine receptor kinase gene family in large cell neuroendocrine carcinoma of the lung." Hum Mutat 29(5): 609-616. (2008).
Martin-Zanca, et al. "A human oncogene formed by the fusion of truncated tropomyosin and protein tyrosine kinase sequences." Nature 319 (6056): 743-748. (Feb. 1986).
Regua, et al. "Trk receptor tyrosine kinases in metastasis and cancer therapy." Discov Med 28(154): 195-203. (published Oct. 21, 2019).
Von Mehren, et al. "Dose escalating study of crenolanib besylate in advanced GIST patients with PDGFRA D842V activating mutations." J Clin Oncol 34 (suppl; abstr 11010). (2016).
United States Patent & Trademark Office (ISA) International Search Report and Written Opinion for PCT/US2021/032685 dated Nov. 17, 2021, 12 pp.
Aikawa, et al. "Quizartinib, a selective FLT3 inhibitor, maintains antileukemic activity in preclinical models of RAS-mediated midostaurin-resistant acute myeloid leukemia cells." Oncotarget 11(11). (Mar. 17, 2020) 943-955.
Amatu, et al. "Tropomyosin receptor kinase (TRK) biology and the role of NTRK gene fusions in cancer." Annals of Oncology 30: viii5-viii15. (Nov. 2019).
Doebele, et al. "Entrectinib in patients with advanced or metastatic NTRK fusion-positive solid tumours: integrated analysis of three phase 1-2 trials." The Lancet Oncology 21(2): 271-282. (Feb. 2020).
Drilon, A. "TRK inhibitors in TRK fusion-positive cancers." Annals of Oncology 30: viii23-viii30. (2019).
Drilon, et al. "Efficacy of Larotrectinib in TRK Fusion-Positive Cancers in Adults and Children." N Engl J Med 378(8): 731-739. (Aug. 22, 2018).

(Continued)

*Primary Examiner* — Raymond J Henley, III
(74) *Attorney, Agent, or Firm* — Edwin S. Flores; Daniel J. Chalker; Chalker Flores, LLP

(57) ABSTRACT

The present invention includes methods for treating TRKA, TRKB, and/or TRKC driven proliferative disorder in a subject comprising administering to the subject a therapeutically effective amount of crenolanib,

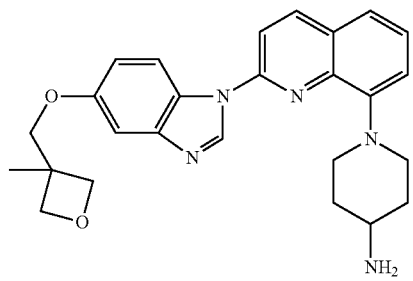

$C_{32}H_{35}N_5O_5S$
Mol. Wt.: 601.72 wherein the subject has a proliferative disorder with overexpression, activation, amplification, or mutation of TRKA, TRKB, and/or TRKC kinase.

21 Claims, 7 Drawing Sheets

(56) References Cited

OTHER PUBLICATIONS

Drilon, et al. "Repotrectinib (TPX-0005) Is a Next-Generation ROS1/TRK/ALK Inhibitor That Potently Inhibits ROS1/TRK/ALK Solvent-Front Mutations." Cancer Discov 8(10): 1227-1236. (Aug. 2018).
Ho, et al. "Resistance to chemotherapy mediated by TrkB in neuroblastomas." Cancer Res 62(22): 6462-6466. (Nov. 15, 2002).
Joshi, et al. "Discovery and characterization of targetable NTRK point mutations in hematologic neoplasms." Blood 135(24): 2159-2170. (Jun. 11, 2020).
Lewis, et al. "Phase 1 study of the safety, tolerability, and pharmacokinetics of oral CP-868,596, a highly specific platelet-derived growth factor receptor tyrosine kinase inhibitor in patients with advanced cancers." J Clin Oncol 27 (31): 5262-5269. (Nov. 1, 2009).
Okamura, et al. "Analysis of NTRK Alterations in Pan-Cancer Adult and Pediatric Malignancies: Implications for NTRK-Targeted Therapeutics." JCO Precis Oncol 2018.
Pacenta, et al. "Entrectinib and other ALK/TRK inhibitors for the treatment of neuroblastoma." Drug Des Devel Ther 12: 3549-3561. (2018).
Smith, et al. "FLT3 D835 mutations confer differential resistance to type II FLT3 inhibitors." Leukemia 29(12): 2390-2392. (Dec. 2015).
Turning Point Therapeutics, I. "Turning Point Therapeutics Reports Early Interim Data from Registrational Phase 2 Trident-1 Study of Repotrectinib, Provides Regulatory Update" Turning Point Therapeutics. (Aug. 19, 2020).

CRENOLANIB FOR TREATING TRK KINASE ASSOCIATED PROLIFERATIVE DISORDERS

CROSS-REFERENCE TO RELATED APPLICATIONS

This application claims priority to U.S. Provisional Application Ser. No. 63/079,585, filed Sep. 17, 2020, the entire contents of which are incorporated herein by reference.

TECHNICAL FIELD OF THE INVENTION

The present invention includes a method of reducing or inhibiting the kinase activity of wild-type and mutant TRK kinases in a cell or a subject, and the use of such compound for treating disorders related to TRKA, TRKB, and/or TRKC.

STATEMENT OF FEDERALLY FUNDED RESEARCH

Not applicable.

INCORPORATION-BY-REFERENCE OF MATERIALS FILED ON COMPACT DISK

Not applicable.

BACKGROUND OF THE INVENTION

Without limiting the scope of the invention, its background is described in connection with its ability to inhibit the tropomyosin receptor (TRK) kinases in the treatment of TRK dependent diseases or conditions.

The TRK kinases, TRKA, TRKB, and TRKC, are involved in a number of normal physiological processes including cell growth and proliferation, neurite outgrowth, pain, and sensory modulation. Each kinase is encoded on a separate gene, NTRK1, NTRK2, and NTRK3, respectively (Amatu, Sartore-Bianchi et al. 2019). In normal signalling, TRK kinases are activated by neurotrophins, including: nerve growth factor (NGF) which activates TRKA; brain derived neurotrophic factor (BDNF) which activates TRKB; neurotrophin 3 (NT-3) which activates TRKA, TRKB, and TRKC; and neurotrophin 4 (NT-4) which activates TRKB (Amatu, Sartore-Bianchi et al. 2019). When a ligand binds the partner TRK receptor kinase, it induces receptor dimerization, autophosphorylation, and downstream signalling, a common activation sequence in receptor tyrosine kinases.

Genetic abnormalities resulting in TRK fusion proteins were first identified in colorectal cancer in 1986 (Martin-Zanca, Hughes et al. 1986). This fusion protein was later determined to be the result of an intrachromosomal rearrangement at 1q22-23, which fused the tropomyosin 3 (TPM3) gene with the kinase domain of TRKA (Amatu, Sartore-Bianchi et al. 2019). Since this discovery, TRK fusions involving TRKA, TRKB, and TRKC have been identified in at least 25 different cancers, with over 80 different fusion partners (Okamura, Boichard et al. 2018, Amatu, Sartore-Bianchi et al. 2019). The majority of identified fusions pair the 5' end of a partner gene encoding one or more dimerization domains with the tyrosine kinase domains of one of the TRK genes. The dimerization of the partner gene sequence results in ligand independent activation of the TRK kinase, leading to dysregulated downstream signalling and cell proliferation.

While the incidence of TRK fusions in most cancer types is very low, there are a number of cancers in which TRK fusions are extremely common. In particular, the ETV6-NTRK3 (TRKC) fusion is found in approximately 90% of mammary-analog secretory carcinoma of the salivary gland, secretory breast carcinoma, and infantile congenital fibrosarcoma. Various TRK fusions involved TRKA, TRKB, or TRKC are also found in approximately 40% of pediatric high-grade glioma in patients younger than 3 years of age (Okamura, Boichard et al. 2018).

In addition to TRK fusions, point mutations with the TRK genes have been identified as driving mutations in a number of different cancers. By example, missense mutations in TRKB including A203T and R458G have been identified in patients with myeloproliferative neoplasms (Joshi, Qian et al. 2020). Mutations within the kinase domain of TRKB and TRKC have also been identified in large cell neuroendocrine carcinoma of the lung (Marchetti, Felicioni et al. 2008).

Finally, other mechanisms of TRK activation including overexpression and copy number gain/amplification have been observed in a number of cancers. In an analysis of The Cancer Genome Atlas (TCGA) and the St. Jude PeCan databases, nonfusion NTRK alterations, including point mutations, amplification, and overexpression were found in approximately 14% of all cancer samples (Okamura, Boichard et al. 2018). More specifically, overexpression of TRKB is associated with poor prognosis in pediatric neuroblastoma and resistance to chemotherapy treatment with doxorubicin, etoposide, and cisplatin (Ho, Eggert et al. 2002, Pacenta and Macy 2018). High expression of TRKB is also associated with poor prognosis in Wilms tumor (Eggert, Grotzer et al. 2001). Increased expression of TRKB is also correlated with aggressive and metastatic disease in breast, laryngeal, colon, and gastric cancers. Finally, TRKC overexpression is common in pancreatic cancer, prostate cancer, leiomyosarcoma, basal cell carcinoma, and cutaneous squamous cell carcinoma, where it is associated with increased epithelial-mesenchymal transition, invasion, and metastasis (Regua, Doheny et al. 2019).

The identification of TRK kinases as driving oncogenes in cancer has spurred the development of TRK kinase inhibitors. To date, two pan-TRK inhibitors have been approved by the Food and Drug Administration for use in TRK fusion positive cancers, agnostic of cancer type, larotrectinib and entrectinib (FDA 2018, FDA 2019). Larotrectinib, the first approved TRK inhibitor, achieved a clinical response in 75% of assessed patients (Drilon, Laetsch et al. 2018). Entrectinib achieved a clinical response in 57% of assessed patients (Doebele, Drilon et al. 2020). Both agents showed efficacy in tumors with TRKA, TRKB, or TRKC fusions. While these response rates are extremely promising, the median progression free survival for entrectinib was 11.1 months, while 45% of patients treated with larotrectinib had progressed within 1 year (Drilon, Laetsch et al. 2018, Drilon 2019, Doebele, Drilon et al. 2020), indicating that additional driving mutations appear during treatment that lead to disease progression.

The acquisition of point mutations within TRK kinases have been identified as a mechanism of resistance to TRK kinase inhibitors. These mutations can be roughly grouped into four classifications: solvent front mutations at TRKA-G595, TRKB-G639, and TRKC-G623; gatekeeper mutations at TRKA-F589, TRKB-F633, and TRKC-F617; xDFG motif mutations at TRKA-G667, TRK-BG709, and TRKC-G696; and other, including TRKA-A608 (Drilon 2019).

These mutations, and possibly others, are resistant to the first-generation pan-TRK inhibitors larotrectinib and entrectinib. While second-generation inhibitors, including repotrectinib and selitrectinb, are currently in development, these agents are in early phase clinical trials and their efficacy in patients has yet to be confirmed, though interim data from a Phase II trial of repotrectinib in ROS mutated or TRK fusion cancers has recently been released (Drilon, Ou et al. 2018, Hyman, Kummar et al. 2019, Turning Point Therapeutics 2020). In addition, TRK inhibitors have yet to be tested in a significant way in patients with other mechanism of TRK activation, such as copy number gain/amplification or overexpression.

Patients with TRK mutations resistant to currently approved therapies represent an unmet need, and the development of additional therapies with activity against both TRK fusions and point mutations within the TRK kinases would be of benefit to patients with TRK associated cancers.

SUMMARY OF THE INVENTION

In one embodiment, the present invention includes a method of inhibiting or reducing TRKA tyrosine kinase activity or expression in a subject suffering from a proliferative disorder or proliferative disease comprising: obtaining a tumor sample from the subject; determining that the proliferative disorder or proliferative disease exhibits one or more of overexpression, activation, amplification, or mutation of TRKA kinase; and administering to the subject a therapeutically effective amount of crenolanib or a pharmaceutically acceptable salt thereof wherein the crenolanib or salt thereof reduces the proliferative disorder burden or prevents proliferative disease progression. In one aspect, the TRKA mutation is a gene fusion. In another aspect, the TRKA gene fusion is selected from one of TFG-TRKA, TPM3-TRKA, TPR-TRKA, BCAN-TRKA, CTRC-TRKA, EPHB2-TRKA, GSN-TRKA, GON4L-TRKA, IRF2BP2-TRKA, LMNA-TRKA, NFASC-TRKA, PDE4DIP-TRKA, PLEXHA6-TRKA, PPL-TRKA, SQSTM1-TRKA, SSBP2-TRKA, or TRIM63-TRKA. In another aspect, the TRKA mutation is a missense, insertion, or deletion mutation. In another aspect, the TRKA mutation is selected from a missense mutation at at least one of A608, F589, L657, or G667C. In another aspect, the proliferative disorder or proliferative disease is selected from at least one of thyroid cancer, colorectal cancer, glioma, sarcoma, glioblastoma, neuroblastoma, Wilms tumor, pancreatic cancer, head and neck cancer, cervical cancer, melanoma, breast cancer, lung cancer, mammary-analog secretory carcinoma of the salivary gland, secretory breast carcinoma, infantile fibrosarcoma, endometrial cancer, gallbladder cancer, gastrointestinal stromal tumor, mesothelioma, multiple myeloma, prostate cancer, leukemia, myeloproliferative disease, myelodysplastic syndrome, idiopathic hypereosinophilic syndrome (HES), bladder cancer, CNS cancer, esophageal cancer, liver cancer, nasopharyngeal cancer, neuroendocrine cancer, ovarian cancer, renal cancer, testicular cancer, cholangiocarcinoma, appendix tumor, and hematologic malignancy. In another aspect, the therapeutically effective amount or crenolanib or the pharmaceutically acceptable salt thereof is from about 50 to 800 mg per day, 100 to 450 mg per day, 200 to 400 mg per day, 300 to 500 mg per day, 350 to 500 mg per day, 400 to 600 mg per day, or 600 to 800 mg per day. In another aspect, the therapeutically effective amount of crenolanib or the pharmaceutically acceptable salt thereof is administered at least one of continuously, intermittently, systemically, or locally. In another aspect, the crenolanib or the pharmaceutically acceptable salt thereof is administered orally, intravenously, topically, intramuscularly, subcutaneously, or intraperitoneally. In another aspect, the crenolanib is a pharmaceutically acceptable salt of crenolanib. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, crenolanib tosylate, crenolanib mesylate, crenolanib benzoate, or crenolanib succinate. In another aspect, the therapeutically effective amount of crenolanib or the pharmaceutically acceptable salt thereof is administered up to three times or more a day for as long as the subject is in need of treatment for a proliferative disease. In another aspect, the therapeutically effective amount of crenolanib or the pharmaceutically acceptable salt thereof is provided at least one of sequentially or concomitantly, with another pharmaceutical agent in a newly diagnosed proliferative disease patient, to maintain remission, or a relapsed/refractory proliferative disease patient. In another aspect, the pharmaceutically acceptable salt thereof is provided as a single agent or in combination with another pharmaceutical agent in a newly diagnosed proliferative disease patient, to maintain remission, or a relapsed/refractory proliferative disease patient. In another aspect, the crenolanib or the pharmaceutically acceptable salt thereof is provided as a single agent or in combination with another pharmaceutical agent in a newly diagnosed proliferative disease pediatric patient, to maintain remission, or a relapsed/refractory proliferative disease pediatric patient.

In another embodiment, the present invention includes a method of inhibiting or reducing TRKB tyrosine kinase activity or expression in a subject suffering from a proliferative disorder or proliferative disease comprising: obtaining a tumor sample from the subject; determining that the proliferative disorder or proliferative disease exhibits one or more of overexpression, activation, amplification, or mutation of TRKB kinase; and administering to the subject a therapeutically effective amount of crenolanib or a pharmaceutically acceptable salt thereof wherein the crenolanib or salt thereof reduces the proliferative disorder burden or prevents proliferative disease progression. In one aspect, the TRKB mutation is a gene fusion. In another aspect, the TRKB gene fusion is selected from one of AFAP1-TRKB, AGBL4-TRKB, NAV1-TRKB, PAN3-TRKB, TRKB-LAP3, SLMAP-TRKB, STRN-TRKB, SQSTM1-TRKB, TRIM24-TRKB, VGL-TRKB, LMNA-TRKB, NOS1AP-TRKB, NAV1-TRKB, STRN-TRKB, KCTD8-TRKB, VCAN-TRKB, CD74-TRKB, OKI-TRKB, TLE4-TRKB, GKAP1-TRKB, TBC1D2-TRKB, DAB2IP-TRKB, TRAF2-TRKB, or ETV6-TRKB. In another aspect, the TRKB mutation is a missense, insertion, or deletion mutation. In another aspect, the TRKB mutation is selected from a missense mutation at least one of F633, G639, or G709. In another aspect, the proliferative disorder or proliferative disease is selected from at least one of thyroid cancer, colorectal cancer, glioma, sarcoma, glioblastoma, neuroblastoma, Wilms tumor, pancreatic cancer, head and neck cancer, cervical cancer, melanoma, breast cancer, lung cancer, mammary-analog secretory carcinoma of the salivary gland, secretory breast carcinoma, infantile fibrosarcoma, endometrial cancer, gallbladder cancer, gastrointestinal stromal tumor, mesothelioma, multiple myeloma, prostate cancer, leukemia, myeloproliferative disease, myelodysplastic syndrome, idiopathic hypereosinophilic syndrome (HES), bladder cancer, CNS cancer, esophageal cancer, liver cancer, nasopharyngeal cancer, neuroendocrine cancer, ovarian cancer, renal cancer, testicular cancer, cholangiocarcinoma, appendix tumor, and hematologic malignancy. In another aspect, the therapeutically effective amount or crenolanib or the pharmaceutically acceptable salt thereof is from about 50 to 800 mg per day, 100 to 450 mg per day, 200 to 400 mg per day, 300 to 500 mg per day, 350 to 500 mg per day, 400 to 600 mg per day, or 600 to 800 mg per day. In another aspect, the therapeutically effective amount of crenolanib or the pharmaceutically acceptable salt thereof is administered at least one of continuously, intermittently, systemically, or locally. In another aspect, the crenolanib or the pharmaceutically acceptable salt thereof is administered orally, intravenously, topically, intramuscularly, subcutaneously, or intraperitoneally. In another aspect, the crenolanib is a pharmaceutically acceptable salt of crenolanib. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, crenolanib tosylate, crenolanib mesylate, crenolanib benzoate, or crenolanib succinate. In another aspect, the therapeutically effective amount of crenolanib or the pharmaceutically acceptable salt thereof is administered up to three times or more a day for as long as the subject is in need of treatment for a proliferative disease. In another aspect, the therapeutically effective amount of crenolanib or the pharmaceutically acceptable salt thereof is provided at least one of sequentially or concomitantly, with another pharmaceutical agent in a newly diagnosed proliferative disease patient, to maintain remission, or a relapsed/refractory proliferative disease patient. In another aspect, the pharmaceutically acceptable salt thereof is provided as a single agent or in combination with another pharmaceutical agent in a newly diagnosed proliferative disease patient, to maintain remission, or a relapsed/refractory proliferative disease patient. In another aspect, the crenolanib or the pharmaceutically acceptable salt thereof is provided as a single agent or in combination with another pharmaceutical agent in a newly diagnosed proliferative disease pediatric patient, to maintain remission, or a relapsed/refractory proliferative disease pediatric patient.

In another embodiment, the present invention includes a method of inhibiting or reducing TRKC tyrosine kinase activity or expression in a subject suffering from a proliferative disease or proliferative disease comprising: obtaining a tumor sample from the subject; determining that the proliferative disorder or proliferative disease exhibits one or more of overexpression, activation, amplification, or mutation of TRKC kinase; and administering to the subject a therapeutically effective amount of crenolanib or a pharmaceutically acceptable salt thereof wherein the crenolanib or salt thereof reduces the proliferative disorder burden or prevents proliferative disease progression. In one aspect, the TRKC mutation is a gene fusion. In another aspect, the TRKC gene fusion is selected from one of AKAP13-TRKC, AML4-TRKC, ETV6-TRKC, FAT1-TRKC, LYN-TRKC, RBPMS-TRKC, TPM4-TRKC, VPS18-TRKC, KHDRBS1-TRKC, IFR2BP2-TRKC, EML4-TRKC, TGF-TRKC, or SQSTM1-TRKC. In another aspect, the TRKC mutation is a missense, insertion, or deletion mutation. In another aspect, the TRKC mutation is selected from a missense mutation at least one of L686 or G696. In another aspect, the proliferative disorder or proliferative disease is selected from at least one of thyroid cancer, colorectal cancer, glioma, sarcoma, glioblastoma, neuroblastoma, Wilms tumor, pancreatic cancer, head and neck cancer, cervical cancer, melanoma, breast cancer, lung cancer, mammary-analog secretory carcinoma of the salivary gland, secretory breast carcinoma, infantile fibrosarcoma, endometrial cancer, gallbladder cancer, gastrointestinal stromal tumor, mesothelioma, multiple myeloma, prostate cancer, leukemia, myeloproliferative disease, myelodysplastic syndrome, idiopathic hypereosinophilic syndrome (HES), bladder cancer, CNS cancer, esophageal cancer, liver cancer, nasopharyngeal cancer, neuroendocrine cancer, ovarian cancer, renal cancer, testicular cancer, cholangiocarcinoma, appendix tumor, and hematologic malignancy. In another aspect, the therapeutically effective amount or crenolanib or the pharmaceutically acceptable salt thereof is from about 50 to 800 mg per day, 100 to 450 mg per day, 200 to 400 mg per day, 300 to 500 mg per day, 350 to 500 mg per day, 400 to 600 mg per day, or 600 to 800 mg per day. In another aspect, the therapeutically effective amount of crenolanib or the pharmaceutically acceptable salt thereof is administered at least one of continuously, intermittently, systemically, or locally. In another aspect, the crenolanib or the pharmaceutically acceptable salt thereof is administered orally, intravenously, topically, intramuscularly, subcutaneously, or intraperitoneally. In another aspect, the crenolanib is a pharmaceutically acceptable salt of crenolanib. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, crenolanib tosylate, crenolanib mesylate, crenolanib benzoate, or crenolanib succinate. In another aspect, the therapeutically effective amount of crenolanib or the pharmaceutically acceptable salt thereof is administered up to three times or more a day for as long as the subject is in need of treatment for a proliferative disease. In another aspect, the therapeutically effective amount of crenolanib or the pharmaceutically acceptable salt thereof is provided at least one of sequentially or concomitantly, with another pharmaceutical agent in a newly diagnosed proliferative disease patient, to maintain remission, or a relapsed/refractory proliferative disease patient. In another aspect, the pharmaceutically acceptable salt thereof is provided as a single agent or in combination with another pharmaceutical agent in a newly diagnosed proliferative disease patient, to maintain remission, or a relapsed/refractory proliferative disease patient. In another aspect, the crenolanib or the pharmaceutically acceptable salt thereof is provided as a single agent or in combination with another pharmaceutical agent in a newly diagnosed proliferative disease pediatric patient, to maintain remission, or a relapsed/refractory proliferative disease pediatric patient.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
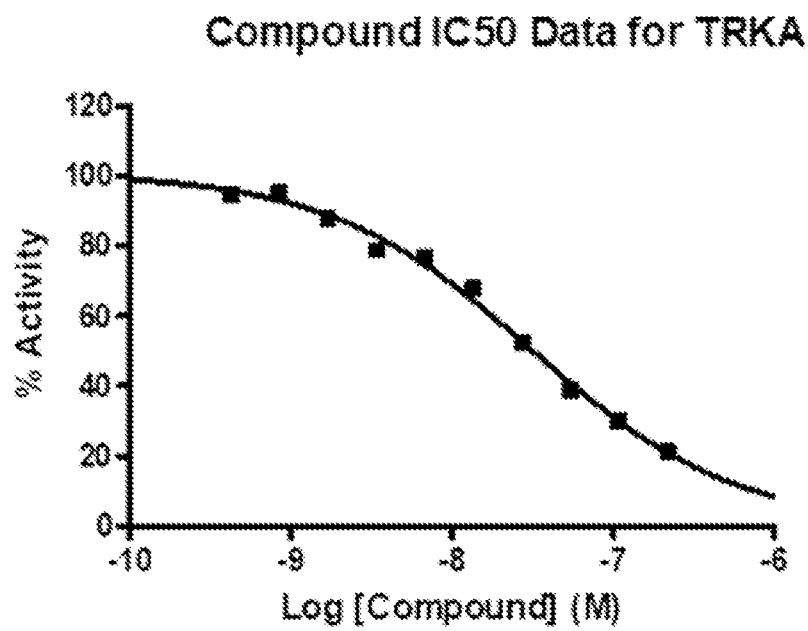
FIG. 1 shows the dose-response curve for IC50 determination of the besylate salt of the present invention for wildtype TRKA. The activity of the besylate salt of crenolanib is plotted against the corresponding molar concentration in log 10 scale.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

The present invention is directed to the administration of crenolanib, or a pharmaceutically acceptable salt thereof, to subjects suffering from a proliferative disease or proliferative disorder in order to treat the disease or disorder, and/or to prevent worsening of the disease or disorder.

Crenolanib is an orally bioavailable TKI. It is significantly more selective for PDGFR, FLT3, and TRK kinases than other kinases, including c-KIT, VEGFR2, TIE2, FGFR2, EGFR, ERBB2, and SRC (Lewis, Lewis et al. 2009, Aikawa, Togashi et al. 2020). As a type 1 TKI which directly interacts with ATP binding pocket, it binds to both the active and inactive conformations of the kinase. Importantly, crenolanib shows clinical activity against FLT3 and PDGFRA mutated proliferative disorders, and has a promising safety profile in both solid tumors and hematological malignancies (von Mehren, Tetzlaff et al. 2016, Goldberg 2020). The preclinical data presented herein confirm that crenolanib also effectively inhibits both wildtype, fusion, and mutant TRK kinases. As such, crenolanib is ideally suited for the treatment of patients suffering from TRK associated proliferative disorders.

The present invention comprises methods of inhibiting wildtype or mutant TRK kinases in a cell or a subject, or to treat disorders related to TRK kinase activity or expression in a subject. In one embodiment, the present invention provides a method for reducing or inhibiting the kinase activity of wildtype or mutant TRK kinases in a subject comprising the step of administering a compound of the present invention to the subject. In other embodiments, the present invention provides therapeutic methods for treating a subject with a cell proliferative disorder driven by aberrant kinase activity of TRK kinases.

Definitions

As used herein, the term "subject" refers to an animal, such as a mammal or a human, who has been the object of treatment, observation or experiment.

As used herein, the term "contacting" refers to the addition of crenolanib or a pharmaceutically available salt(s) thereof, to cells such that the compound is taken up by the cell.

As used herein, the term "therapeutically effective amount" refers to an amount of crenolanib or pharmaceutically acceptable salt(s) thereof, that elicits the biological or medicinal response in a subject that is being sought by a researcher, veterinarian, medical doctor or other clinician, which includes alleviation of the symptoms of the disease or the disorder being treated, reduction in the burden of the proliferative 5 disorder (such as reduction in tumor size), and/or increase in progression-free or overall survival including prolonged stable disease. Methods for determining therapeutically effective doses for pharmaceutical compositions comprising a compound of the present invention are known in the art.

As used herein, the term "composition" is intended to encompass a product comprising the specified ingredients in the specified amounts, as well as any product which results, directly or indirectly, from combinations of the specified ingredients in the specified amounts.

As used herein, the terms "disorder related to TRK kinase activity", or "TRK kinase driven cell proliferative disorder" includes diseases associated or implicating aberrant TRK kinase activity, for example, overexpression, fusion, or mutations of TRKA, TRKB, or TRKC.

As used herein, the term "cell proliferative disorders" refers to excess cell proliferation of one or more subset of cells in a multicellular organism resulting in harm (i.e. discomfort or decreased life expectancy) to the multicellular organism. Cell proliferative disorders can occur in different types of animals and humans. Examples of cell proliferative disorders are thyroid cancer, colorectal cancer, glioma, sarcoma, glioblastoma, neuroblastoma, Wilms tumor, pancreatic cancer, head and neck cancer, cervical cancer, melanoma, breast cancer, lung cancer, mammary-analog secretory carcinoma of the salivary gland, secretory breast carcinoma, infantile fibrosarcoma, endometrial cancer, gallbladder cancer, gastrointestinal stromal tumor, mesothelioma, multiple myeloma, prostate cancer, leukemia, myeloproliferative disease, myelodysplastic syndrome, idiopathic hypereosinophilic syndrome (HES), bladder cancer, CNS cancer, esophageal cancer, liver cancer, nasopharyngeal cancer, neuroendocrine cancer, ovarian cancer, renal cancer, testicular cancer, cholangiocarcinoma, appendix tumor, and hematologic malignancy.

As used herein, the term "relapsed/refractory" refers to a subject that was previously administered a pharmaceutical agent in order to treat a proliferative disease, but either did not respond to treatment (refractory), or progressed after initially responding (relapsed).

Detection of the mutated TRK kinases can be performed using any suitable means known in the art. For example, detection of gene mutations can be accomplished by detecting nucleic acid molecules (such as DNA) using nucleic acid amplification methods (such as RT-PCR) or high-throughput sequencing (i.e. "next-generation sequencing"). By example, next-generation sequencing platforms such as Illumina may be used to determine the exact genetic sequence of specific genes, or portions of genes, of interest. In brief, DNA from a tumor sample is fragmented, ligated with the appropriate primers and adaptors, and amplified using PCR during "library preparation". The prepared libraries are then sequenced using one of a number of commercially available systems which generates the sequence of the chosen target genes, all exomes, or the entire genome. The sequences are then analyzed using commercial available software, which aligns the tumor sample sequence to the known sequence of the genes of interest and performs a variant calling step, which identifies differences at the DNA level in the tumor sample and determines if such mutations would result in alteration of the amino acid sequence in the translated protein. Using these systems, a person of skill in the art can determine if a subject has one of the identified mutations with in one of the TRK genes (NTRK1, NTRK2, or NTRK3). For determination of variants and mutations, the following gene and protein accession numbers may be used, the database is listed in parentheses after the accession number: TRKA, NM_002529.3 (GenBank), NP_002520.2 (GenPept), P04629-1 (UniProt); TRKB, NM_001018064.2 (GenBank), NP_001018074.1 (GenPept), Q16620-1 (UniProt); TRKC, NM_001012338.2 (GenBank), NP_001012338.1 (GenPept), Q16288-1 (UniProt).

Detection of fusion, amplified, or copy number gain, TRK kinases, amplified TRK kinases, can be performed using any suitable means known in the art. For example, detection of fusion genes may be performed using next-generation sequencing methods, immunohistochemistry, in-situ hybridization methods, or karyotype analysis.

As used herein, the term "overexpression" or "overexpressed" refers to an increased level of transcription of the gene as compared to the expression levels in a control (e.g. a non-cancerous cell of the same cell type). Detection of overexpression or activation of TRK kinases can be performed using any suitable means known in the art. For example, detection of overexpress or activated TRK kinases may be performed using immunohistochemistry, quantitative RT-PCR, or western blot analysis.

As used herein, the term "fusion" refers to alterations in the genetic sequence, typically as a result of translocation or inversion within a chromosome or between multiple chromosomes, which results in the pairing of the kinase domain of one of the TRK kinases with a partner gene in the translated protein sequence.

As used herein, the term "missense mutation" refers to a nucleotide mutation in the DNA sequence which results in an amino acid substitution at the protein level.

As used herein, the terms "resistance mutations", or "mutations conferring resistance", or "secondary mutations" refer to mutations within the TRKA, TRKB, and/or TRKC genes which are not sensitive to larotrectinib, entrectinib, or other TKIs other than the present invention. In other words, these mutations, present alone or in combination with other TRK alterations such as fusions retain kinase activity when treated with larotrectinib, entrectinib, or other TKIs, but are inhibited by the present invention. Non-limiting examples of resistance mutations are missense mutations at amino acid residues: A608, F589, L657, or G667C within TRKA; F633, G639, or G709 within TRKB; and/or L686 or G696 within TRKC. Additional mutations within the gatekeeper, xDFG, and other domains are included in the scope of the present invention.

As used herein, the term "solvent front" or "solvent front mutations" refers to mutations at amino acid residues G595, G639, and G623 in TRKA, TRKB, and TRKC, respectively. These residues sit at the front of the ATP binding pocket, extending into the cytoplasm of the cell, and mutations resulting in the substitution of larger or charged amino acids results in a conformational change that prevents drug binding of larotrectinib and entrectinib, conferring resistance to these agents.

As used herein, the term "gatekeeper" or "gatekeeper mutations" refers to mutations at amino acid residues F589, F633, and F617 in TRKA, TRKB, and TRKC, respectively. These residues sit at the top of the ATP binding pocket, and mutations resulting in substitution of larger amino acids can block drug binding of larotrectinib and entrectinib, conferring resistance to these agents. As detailed herein, the present invention is able to overcome these mutations.

As used herein, the term "xDFG" or "xDFG mutations" refers to mutations at amino acid residues G667, G709, and G696 in TRKA, TRKB, and TRKC as well as the residues immediately surrounding these amino acids (e.g. D668 and F669 in TRKA). These residues sit at the back of the ATP binding pocket. In the inactive conformation, the DFG motif blocks access to the ATP binding pocket. In the active conformation, the DGF motif is pulled to the back of the pocket, allowing binding of ATP. The substitution of hydrophobic amino acids results in an active conformation and constitutive activation of the kinase. These mutations are analogous to FLT3-D835 mutations, which the present invention is exceptionally active against (Smith, Lin et al. 2015).

As used herein, the term "other" or "other mutations" refers to mutations in TRKA, TRKB, or TRKC which are not specifically solvent front, gatekeeper, or xDFG mutations. Non-limiting examples of such mutations are TRKA-L657, TRKA-A608, and TRKC-L686. Mutations included in the scope of the present invention are mutations in the kinase domains, the hinge region, the juxtamembrane domain, and the extracellular domain.

In one embodiment, the present invention comprises therapeutically effective amounts of the compound having Formula I:

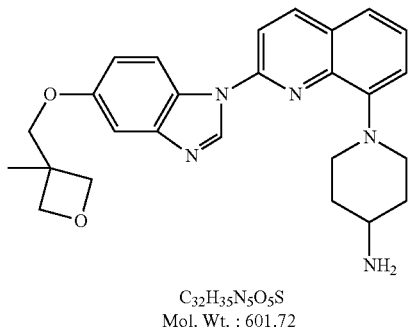 [SMILES: CC1(COc2ccc3c(c2)ncn3-c2ccc3cccc(N4CCC(N)CC4)c3n2)COC1 ; "C32H35N5O5S"]

$C_{32}H_{35}N_5O_5S$
Mol. Wt. : 601.72 or a pharmaceutically acceptable salt or solvate thereof, in a therapeutically effect amount against a proliferative disease that is selected from at least one of thyroid cancer, colorectal cancer, glioma, sarcoma, glioblastoma, neuroblastoma, Wilms tumor, pancreatic cancer, head and neck cancer, cervical cancer, melanoma, breast cancer, lung cancer, mammary-analog secretory carcinoma of the salivary gland, secretory breast carcinoma, infantile fibrosarcoma, endometrial cancer, gallbladder cancer, gastrointestinal stromal tumor, mesothelioma, multiple myeloma, prostate cancer, leukemia, myeloproliferative disease, myelodysplastic syndrome, idiopathic hypereosinophilic syndrome (HES), bladder cancer, CNS cancer, esophageal cancer, liver cancer, nasopharyngeal cancer, neuroendocrine cancer, ovarian cancer, renal cancer, testicular cancer, cholangiocarcinoma, appendix tumor, and hematologic malignancy. Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention, including Crenolanib as Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate.

Compounds of the present invention may be administered to a subject systemically, for example, orally, topically, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 50 to 500 mg per adult human per day. For oral administration, the compositions are preferably provided in the form of tablets containing 20 and 100 milligrams. The compounds of the present invention may be administered on a regimen up to three times or more per day. Preferably three times per day. Optimal doses to be administered may be determined by those skilled in the art, and will vary with the compound of the present invention used, the mode of administration, the time of administration, the strength of the preparation, the details of the disease condition. Factors associated with patient characteristics, such as age, weight, and diet will call for dosage adjustments. Mother examples, the daily dosage of the compounds of the present invention may be varied over a wide range from 15 to 500, 25 to 450, 50 to 400, 100 to 350, 150 to 300, 200 to 250, 15, 25, 50, 75, 100, 150, 200, 250, 300, 400, 450, or 500 mg per day. The compounds of the present invention may be administered on a daily regimen, once, twice, three or more times per day. Optimal doses to be administered may be determined by those skilled in the art, and will vary with the compound of the present invention used, the mode of administration, the time of administration, the strength of the preparation, the details of the disease condition. One or more factors associated with subject characteristics, such as age, weight, and diet will call for dosage adjustments. Techniques and compositions for making useful dosage forms using the Crenolanib are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); relevant portions incorporated herein by reference.

A dosage unit for use of Crenolanib, may be a single compound or mixtures thereof with other compounds, e.g., a potentiator. The compounds may be mixed together, form ionic or even covalent bonds. The compounds of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the Crenolanib of the present invention to a patient in need of therapy.

The Crenolanib is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the Crenolanib may be formulated to provide, e.g., maximum and/or consistent dosing for the particular form for oral, rectal, topical, intravenous injection or parenteral administration. While the Crenolanib may be administered alone, it will generally be provided in a stable salt form mixed with a pharmaceutically acceptable carrier. The carrier may be solid or liquid, depending on the type and/or location of administration selected.

Preparation of the compounds of the present invention. General synthetic methods, which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention.

Biological Activity

In vitro Assays. The following representative in vitro assays were performed in determining the TRKA/TRKB/TRKC biological activity of the present invention. These are given to illustrate the invention in a non-limiting fashion.

Inhibition of wildtype and mutant TRK enzyme activity exemplifies the specific inhibition of the wildtype and mutant TRK enzyme and cellular processes that are dependent on TRK activity. All of the examples herein show significant and specific inhibition of wildtype and mutant TRK kinase and TRK-dependent cellular responses.

Direct enzyme phosphorylation assay. The Reaction Biology HotSpot Kinase assay was used to screen the present invention against a panel of normal TRKA, TRKB, and TRKC and mutated TRK kinases. For assays of all kinases, the TRK enzyme was prepared in base reaction buffer (20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO). The reaction was initiated by the addition of 33P-ATP (10 µCi/µL) into the mixture. The reaction mixture was incubated for 120 minutes at room temperature. Radioactivity was detected by filter-binding method, and kinase activity expressed as the percent remaining kinase activity in test samples compared to vehicle reactions. IC50 values and curve fitting were obtained using Prism (GraphPad Software).

Figure 2:
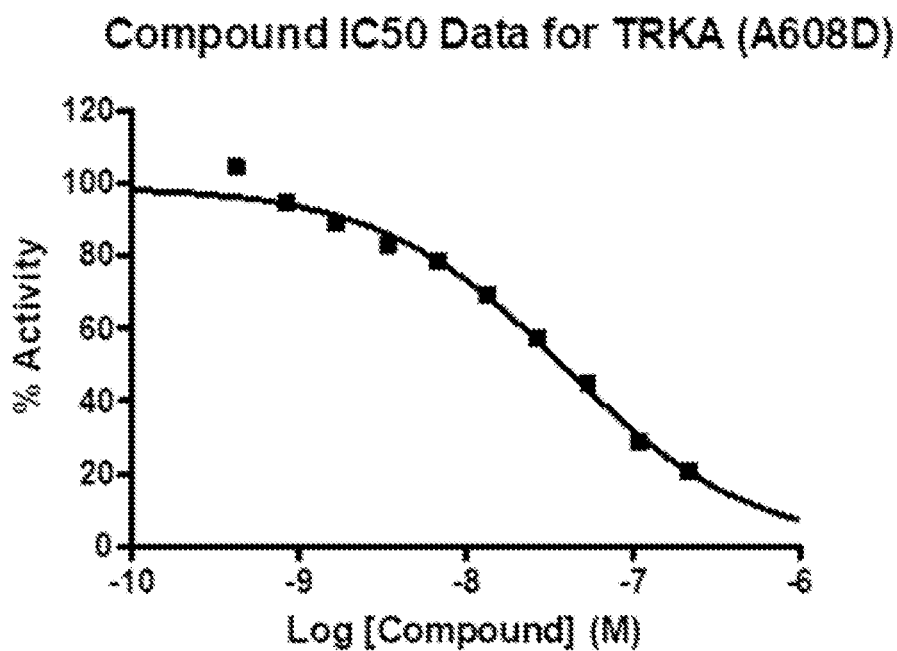
FIG. 2 shows the dose-response curve for IC50 determination of the besylate salt of the present invention for TRKA-A608D. The activity of the besylate salt of crenolanib is plotted against the corresponding molar concentration in log 10 scale.
Figure 3:
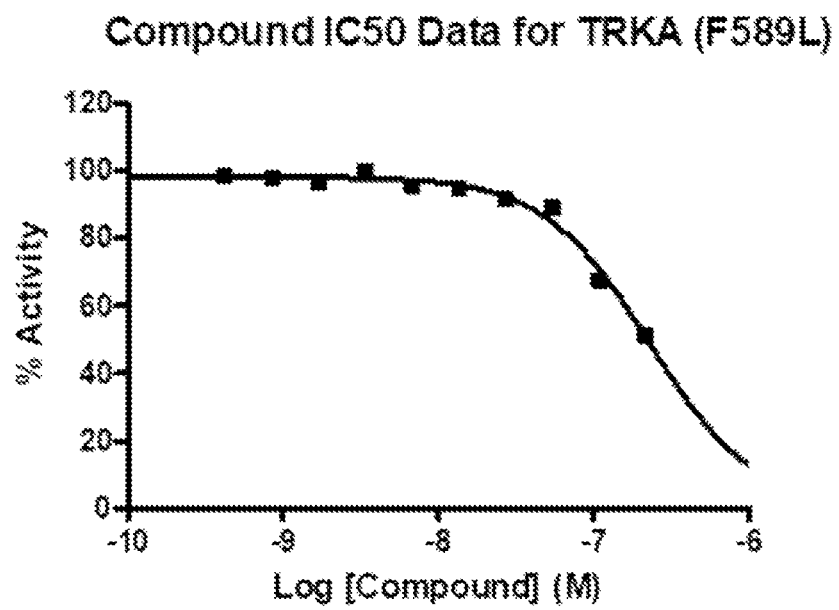
FIG. 3 shows the dose-response curve for IC50 determination of the besylate salt of the present invention for TRKA-D589L. The activity of the besylate salt of crenolanib is plotted against the corresponding molar concentration in log 10 scale.
Figure 4:
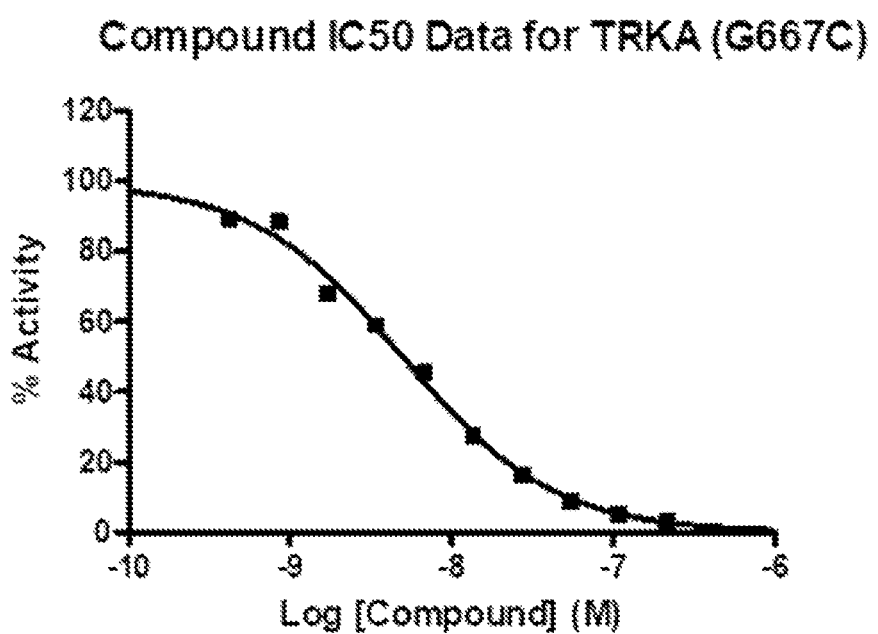
FIG. 4. shows the dose-response curve for IC50 determination of the besylate salt of the present invention for TRKA-G667C. The activity of the besylate salt of crenolanib is plotted against the corresponding molar concentration in log 10 scale.
Figure 5:
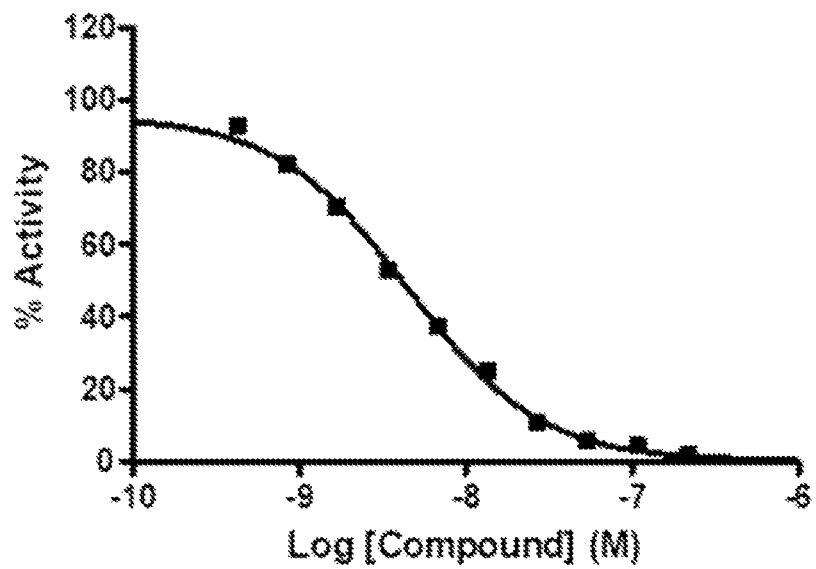
FIG. 5 shows the dose-response curve for IC50 determination of the besylate salt of the present invention for TRKA-G667S. The activity of the besylate salt of crenolanib is plotted against the corresponding molar concentration in log 10 scale.
Figure 6:
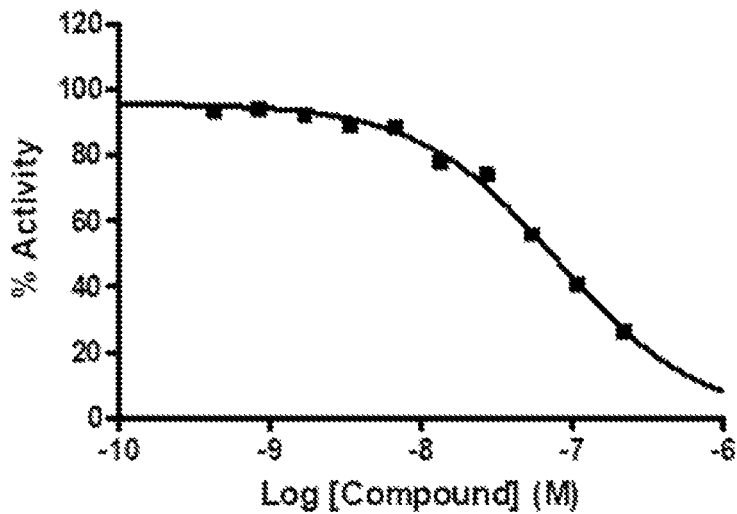
FIG. 6 shows the dose-response curve for IC50 determination of the besylate salt of the present invention for TRKA-L657M. The activity of the besylate salt of crenolanib is plotted against the corresponding molar concentration in log 10 scale.
Figure 7:
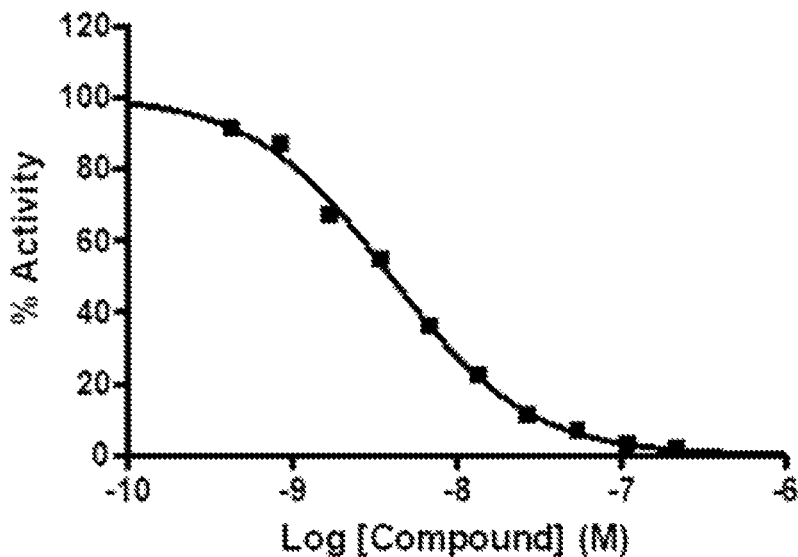
FIG. 7 shows the dose-response curve for IC50 determination of the besylate salt of the present invention for the TRKA-TFG fusion. The activity of the besylate salt of crenolanib is plotted against the corresponding molar concentration in log 10 scale.
Figure 8:
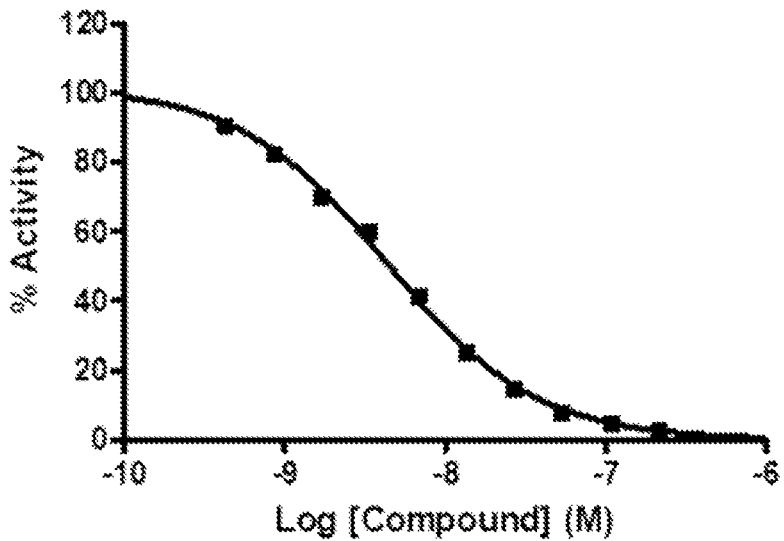
FIG. 8 shows the dose-response curve for IC50 determination of the besylate salt of the present invention for the TRKA-TPM3 fusion. The activity of the besylate salt of crenolanib is plotted against the corresponding molar concentration in log 10 scale.
Figure 9:
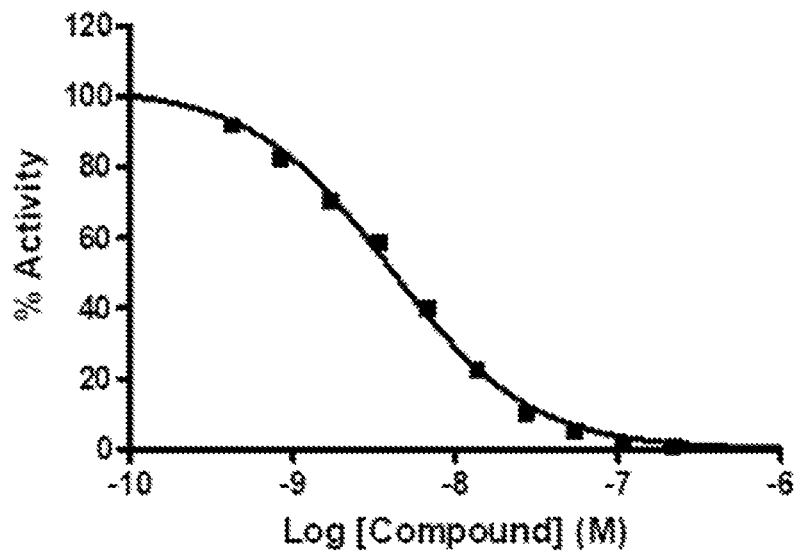
FIG. 9 shows the dose-response curve for IC50 determination of the besylate salt of the present invention for the TRKA-TPR fusion. The activity of the besylate salt of crenolanib is plotted against the corresponding molar concentration in log 10 scale.
Figure 10:
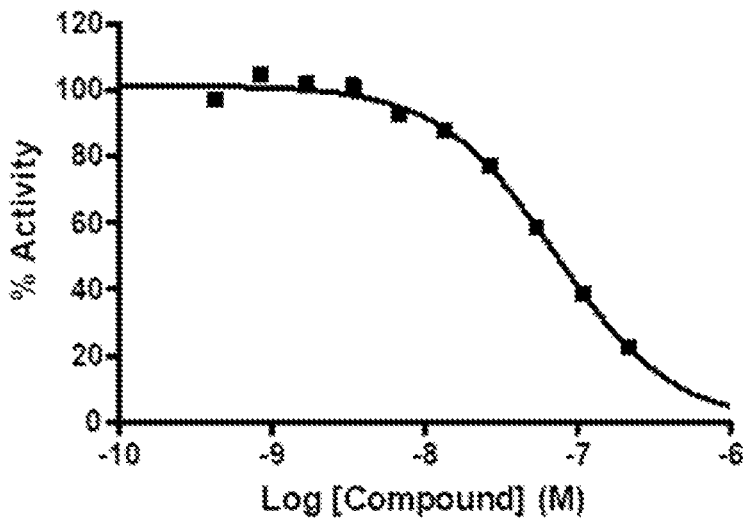
FIG. 10 shows the dose-response curve for IC50 determination of the besylate salt of the present invention for wildtype TRKB. The activity of the besylate salt of crenolanib is plotted against the corresponding molar concentration in log 10 scale.
Figure 11:
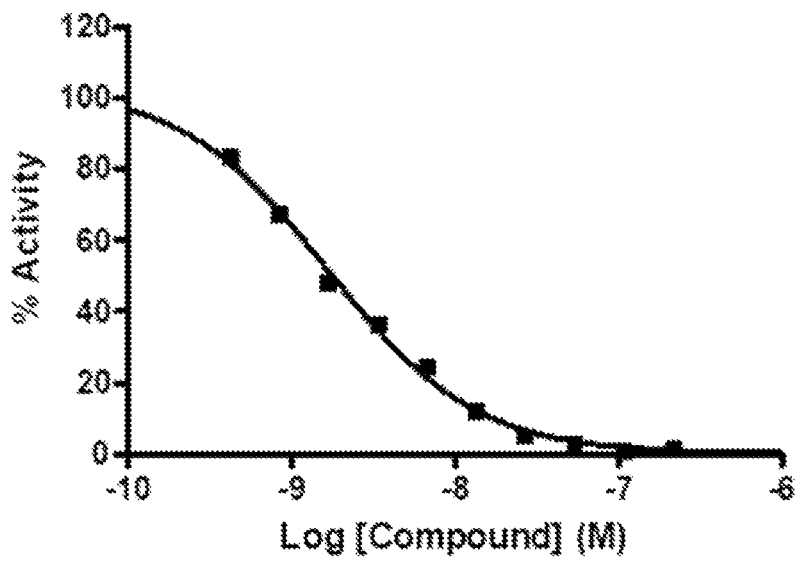
FIG. 11 shows the dose-response curve for IC50 determination of the besylate salt of the present invention for wildtype TRKC. The activity of the besylate salt of crenolanib is plotted against the corresponding molar concentration in log 10 scale.
Figure 12:
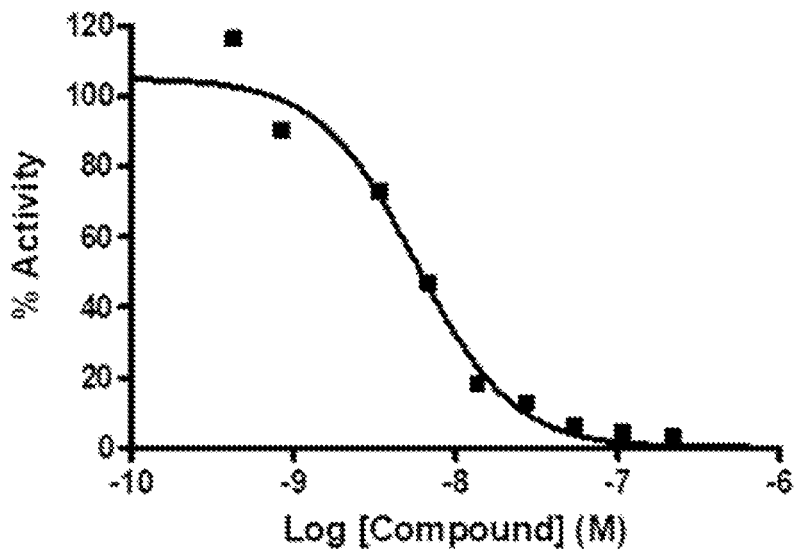
FIG. 12 shows the dose-response curve for IC50 determination of the besylate salt of the present invention for TRKC-G696A. The activity of the besylate salt of crenolanib is plotted against the corresponding molar concentration in log 10 scale.
Figure 13:
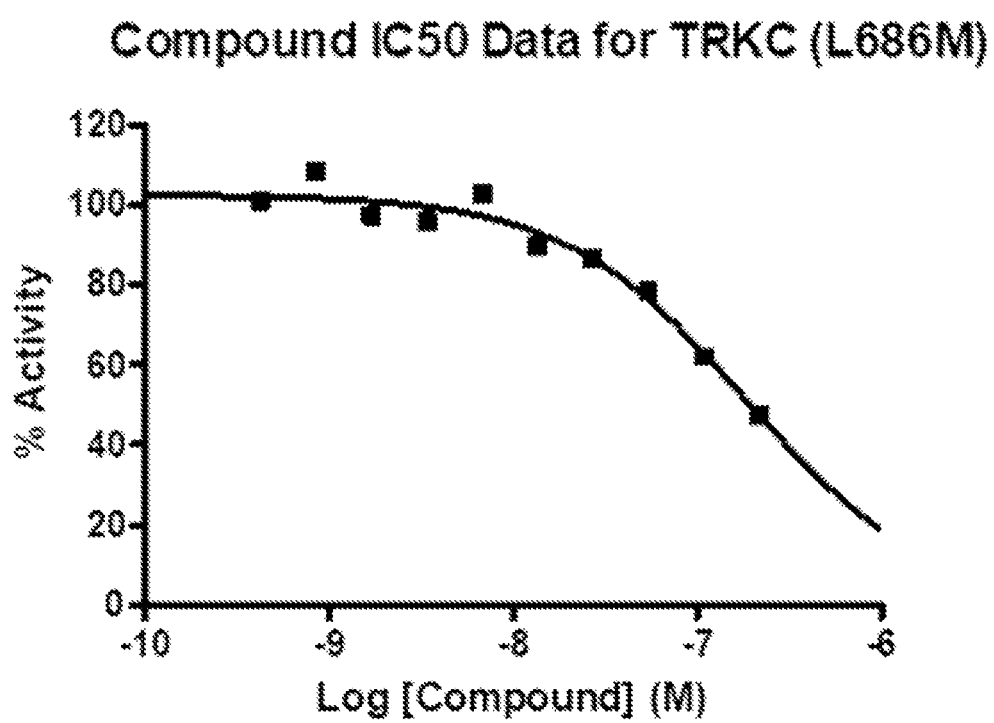
FIG. 13 shows the dose-response curve for IC50 determination of the besylate salt of the present invention for TRKC-L686M. The activity of the besylate salt of crenolanib is plotted against the corresponding molar concentration in log 10 scale.

The activity of the besylate salt of the present invention was determined using a direct enzymatic Reaction Biology HotSpot Kinase assay. All IC50 values are presented in nanomolar concentration. In the direct enzymatic measurement assay, the IC50 of the besylate salt of the current invention against the various TRK kinases is shown in Table 1. The activity of the besylate salt of the present invention against these kinases is also displayed in FIGS. 1 to 13.

TABLE 1

| Classification | Kinase | IC50 (nM) |
| --- | --- | --- |
| Wildtype | TRKA | 31.0 |
| Fusion | TRKA-TFG | 3.95 |
|  | TRKA-TPM3 | 4.34 |
|  | TRKA-TPR | 3.98 |
| xDFG Mutant | TRKA-G667C | 5.0 |
|  | TRKA-G667S | 4.52 |
| Other Mutant | TRKA-L657M | 79.7 |
|  | TRKA-A608D | 38.7 |

TABLE 1-continued

| Classification | Kinase | IC50 (nM) |
| --- | --- | --- |
| Wildtype | TRKB | 77.7 |
| Wildtype | TRKC | 1.68 |
| xDFG Mutant | TRKC-G696A | 5.69 |
| Other Mutant | TRKC-L686M | 184 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±0.1, 0.5, 1, 2, 3, 4, 5, 6, 7, 10, 12 or 15%, or as understood to be within a normal tolerance in the art, for example, within 2 standard deviations of the mean. Unless otherwise clear from the context, all numerical values provided herein are modified by the term about.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Aikawa, T., N. Togashi, K. Iwanaga, H. Okada, Y. Nishiya, S. Inoue, M. J. Levis and T. Isoyama (2020). "Quizartinib, a selective FLT3 inhibitor, maintains antileukemic activity in preclinical models of RAS-mediated midostaurin-resistant acute myeloid leukemia cells." Oncotarget 11(11).

Amatu, A., A. Sartore-Bianchi, K. Bencardino, E. G. Pizzutilo, F. Tosi and S. Siena (2019). "Tropomyosin receptor kinase (TRK) biology and the role of NTRK gene fusions in cancer." Annals of Oncology 30: viii5-viii15.

Doebele, R. C., A. Drilon, L. Paz-Ares, S. Siena, A. T. Shaw, A. F. Farago, C. M. Blakely, T. Seto, B. C. Cho, D. Tosi, B. Besse, S. P. Chawla, L. Bazhenova, J. C. Krauss, Y. K. Chae, M. Barve, I. Garrido-Laguna, S. V. Liu, P. Conkling, T. John, M. Fakih, D. Sigal, H. H. Loong, G. L. Buchschacher, P. Garrido, J. Nieva, C. Steuer, T. R. Overbeck, D. W. Bowles, E. Fox, T. Riehl, E. Chow-Maneval, B. Simmons, N. Cui, A. Johnson, S. Eng, T. R. Wilson and G. D. Demetri (2020). "Entrectinib in patients with advanced or metastatic NTRK fusion-positive solid tumours: integrated analysis of three phase 1-2 trials." The Lancet Oncology 21(2): 271-282.

Drilon, A. (2019). "TRK inhibitors in TRK fusion-positive cancers." Annals of Oncology 30: viii23-viii30.

Drilon, A., T. W. Laetsch, S. Kummar, S. G. DuBois, U. N. Lassen, G. D. Demetri, M. Nathenson, R. C. Doebele, A. F. Farago, A. S. Pappo, B. Turpin, A. Dowlati, M. S. Brose, L. Mascarenhas, N. Federman, J. Berlin, W. S. El-Deiry, C. Baik, J. Deeken, V. Boni, R. Nagasubramanian, M. Taylor, E. R. Rudzinski, F. Meric-Bernstam, D. P. S. Sohal, P. C. Ma, L. E. Raez, J. F. Hechtman, R. Benayed, M. Ladanyi, B. B. Tuch, K. Ebata, S. Cruickshank, N. C. Ku, M. C. Cox, D. S. Hawkins, D. S. Hong and D. M. Hyman (2018). "Efficacy of Larotrectinib in TRK Fusion-Positive Cancers in Adults and Children." N Engl J Med 378(8): 731-739.

Drilon, A., S. I. Ou, B. C. Cho, D. W. Kim, J. Lee, J. J. Lin, V. W. Zhu, M. J. Ahn, D. R. Camidge, J. Nguyen, D. Zhai, W. Deng, Z. Huang, E. Rogers, J. Liu, J. Whitten, J. K. Lim, S. Stopatschinskaja, D. M. Hyman, R. C. Doebele, J. J. Cui and A. T. Shaw (2018). "Repotrectinib (TPX-0005) Is a Next-Generation ROS1/TRK/ALK Inhibitor That Potently Inhibits ROS1/TRK/ALK Solvent-Front Mutations." Cancer Discov 8(10): 1227-1236.

Eggert, A., M. A. Grotzer, N. Ikegaki, H. Zhao, A. Cnaan, G. M. Brodeur and A. E. Evans (2001). "Expression of the neurotrophin receptor TrkB is associated with unfavorable outcome in Wilms' tumor." J Clin Oncol 19(3): 689-696.

FDA (2018). Larotrectinib Label (2018).

FDA (2019). Entrectinib Label (2019).

Goldberg, A. (2020). Younger Patients with Newly Diagnosed FLT3-Mutant AML Treated with Crenolanib Plus Chemotherapy Achieve Durable Remissions. EHA.

Ho, R., A. Eggert, T. Hishiki, J. E. Minturn, N. Ikegaki, P. Foster, A. M. Camoratto, A. E. Evans and G. M. Brodeur (2002). "Resistance to chemotherapy mediated by TrkB in neuroblastomas." Cancer Res 62(22): 6462-6466.

Hyman, D., S. Kummar, A. Farago, B. Geoerger, M. Mau-Sorensen, M. Taylor, E. Garralda, R. Nagasubramanian, M. Natheson, L. Song, M. Capra, M. Jorgensen, A. Ho, N. Shukla, S. Smith, X. Huang, B. Tuch, N. Ku, T. W. Laetsch, A. Drilon and D. Hong (2019). "Abstract CT127: Phase I and expanded access experience of LOXO-195 (BAY 2731954), a selective next-generation TRK inhibitor (TRKi)." Cancer Research 79(13 Supplement): CT127-CT127.

Joshi, S. K., K. Qian, W. H. Bisson, K. Watanabe-Smith, A. Huang, D. Bottomly, E. Traer, J. W. Tyner, S. K. McWeeney, M. A. Davare, B. J. Druker and C. E. Tognon (2020). "Discovery and characterization of targetable NTRK point mutations in hematologic neoplasms." Blood 135(24): 2159-2170.

Lewis, N. L., L. D. Lewis, J. P. Eder, N. J. Reddy, F. Guo, K. J. Pierce, A. J. Olszanski and R. B. Cohen (2009). "Phase I study of the safety, tolerability, and pharmacokinetics of oral CP-868,596, a highly specific platelet-derived growth factor receptor tyrosine kinase inhibitor in patients with advanced cancers." J Clin Oncol 27(31): 5262-5269.

Marchetti, A., L. Felicioni, G. Pelosi, M. Del Grammastro, C. Fumagalli, M. Sciarrotta, S. Malatesta, A. Chella, F. Barassi, F. Mucilli, P. Camplese, T. D'Antuono, R. Sacco and F. Buttitta (2008). "Frequent mutations in the neurotrophic tyrosine receptor kinase gene family in large cell neuroendocrine carcinoma of the lung." Hum Mutat 29(5): 609-616.

Martin-Zanca, D., S. H. Hughes and M. Barbacid (1986). "A human oncogene formed by the fusion of truncated tropomyosin and protein tyrosine kinase sequences." Nature 319(6056):743-748.

Okamura, R., A. Boichard, S. Kato, J. K. Sicklick, L. Bazhenova and R. Kurzrock (2018). "Analysis of NTRK Alterations in Pan-Cancer Adult and Pediatric Malignancies: Implications for NTRK-Targeted Therapeutics." JCO Precis Oncol 2018.

Pacenta, H. L. and M. E. Macy (2018). "Entrectinib and other ALK/TRK inhibitors for the treatment of neuroblastoma." Drug Des Devel Ther 12: 3549-3561.

Regua, A. T., D. Doheny, A. Arrigo and H. W. Lo (2019). "Trk receptor tyrosine kinases in metastasis and cancer therapy." Discov Med 28(154): 195-203.

Smith, C. C., K. Lin, A. Stecula, A. Sali and N. P. Shah (2015). "FLT3 D835 mutations confer differential resistance to type II FLT3 inhibitors." Leukemia 29(12): 2390-2392.

Turning Point Therapeutics, I. (2020). Turning Point Therapeutics Reports Early Interim Data from Registrational Phase 2 Trident-1 Study of Repotrectinib, Proivdes Regulatory Update. Turning Point Therapeutics.

von Mehren, M., E. D. Tetzlaff, M. Macaraeg, J. Davis, A. Vartika, R. Abhijit and M. C. Heinrich (2016). "Dose escalating study of crenolanib besylate in advanced GIST patients with PDGFRA D842V activating mutations." J Clin Oncol 34 (suppl; abstr 11010).

What is claimed is:

1. A method of inhibiting or reducing a TRKA tyrosine kinase activity or expression thereof in a subject suffering from a proliferative disorder or proliferative disease comprising:
   determining that the proliferative disorder or proliferative disease that has at least one of: overexpression, activation, amplification, or mutation of TRKA kinase; and administering to the subject a therapeutically effective amount of crenolanib or a pharmaceutically acceptable salt thereof wherein the crenolanib or salt thereof inhibits or reduces the TRKA tyrosine kinase activity or reduces expression of the TRKA tyrosine kinase activity in a subject suffering from a proliferative disorder or proliferative disease.

2. The method of claim 1, wherein the TRKA mutation is at least one of: a gene fusion; a TRKA gene fusion selected from one of TFG-TRKA, TPM3-TRKA, TPR-TRKA, BCAN-TRKA, CTRC-TRKA, EPHB2-TRKA, GON4L-TRKA, GSN-TRKA, IRF2BP2-TRKA, LMNA-TRKA, NFASC-TRKA, PDE4DIP-TRKA, PLEKHA6-TRKA, PPL-TRKA, SQSTM1-TRKA, SSBP2-TRKA, or TRIM63-TRKA; a missense, insertion, or deletion mutation; or a missense mutation at at least one of A608, F589, L657, or G667C.

3. The method of claim 1, wherein the proliferative disorder or proliferative disease is selected from at least one of thyroid cancer, colorectal cancer, glioma, sarcoma, glioblastoma, neuroblastoma, Wilms tumor, pancreatic cancer, head and neck cancer, cervical cancer, melanoma, breast cancer, lung cancer, mammary-analog secretory carcinoma of the salivary gland, secretory breast carcinoma, infantile fibrosarcoma, endometrial cancer, gallbladder cancer, gastrointestinal stromal tumor, mesothelioma, multiple myeloma, prostate cancer, leukemia, myeloproliferative disease, myelodysplastic syndrome, idiopathic hypereosinophilic syndrome (HES), bladder cancer, CNS cancer, esophageal cancer, liver cancer, nasopharyngeal cancer, neuroendocrine cancer, ovarian cancer, renal cancer, testicular cancer, cholangiocarcinoma, appendix tumor, and hematologic malignancy.

4. The method of claim 1, wherein the therapeutically effective amount or crenolanib or the pharmaceutically acceptable salt thereof is from about 50 to 800 mg per day, 100 to 450 mg per day, 200 to 400 mg per day, 300 to 500 mg per day, 350 to 500 mg per day, 400 to 600 mg per day, or 600 to 800 mg per day.

5. The method of claim 1, wherein the therapeutically effective amount of crenolanib or the pharmaceutically acceptable salt thereof is at least one of:
   administered at least one of continuously, intermittently, systemically, or locally;
   administered orally, intravenously, topically, intramuscularly, subcutaneously, or intraperitoneally;
   administered up to three times or more a day for as long as the subject is in need of treatment for a proliferative disease;
   administered at least one of sequentially or concomitantly, with another pharmaceutical agent in a newly diagnosed proliferative disease patient, to maintain remission, or a relapsed/refractory proliferative disease patient;

administered as a single agent or in combination with another pharmaceutical agent in a newly diagnosed proliferative disease patient, to maintain remission, or a relapsed/refractory proliferative disease patient; or administered as a single agent or in combination with another pharmaceutical agent in a newly diagnosed proliferative disease pediatric patient, to maintain remission, or a relapsed/refractory proliferative disease pediatric patient.

6. The method of claim 1, wherein the crenolanib is a pharmaceutically acceptable salt of crenolanib.

7. The method of claim 1, wherein the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, crenolanib tosylate, crenolanib mesylate, crenolanib benzoate, or crenolanib succinate.

8. A method of inhibiting or reducing a TRKB tyrosine kinase activity or expression thereof in a subject suffering from a proliferative disorder or proliferative disease comprising:
determining that the proliferative disorder or proliferative disease that has at least one of: overexpression, activation, amplification, or mutation of TRKB kinase; and
administering to the subject a therapeutically effective amount of crenolanib or a pharmaceutically acceptable salt thereof inhibits or reduces the TRKB tyrosine kinase activity or reduces expression of the TRKB tyrosine kinase activity in a subject suffering from a proliferative disorder or proliferative disease.

9. The method of claim 8, wherein the TRKA mutation is at least one of: a gene fusion; a TRKA gene fusion selected from one of TFG-TRKA, TPM3-TRKA, TPR-TRKA, BCAN-TRKA, CTRC-TRKA, EPHB2-TRKA, GON4L-TRKA, GSN-TRKA, IRF2BP2-TRKA, LMNA-TRKA, NFASC-TRKA, PDE4DIP-TRKA, PLEKHA6-TRKA, PPL-TRKA, SQSTM1-TRKA, SSBP2-TRKA, or TRIM63-TRKA; a missense, insertion, or deletion mutation; or a missense mutation at at least one of A608, F589, L657, or G667C.

10. The method of claim 8, wherein the proliferative disorder or proliferative disease is selected from at least one of thyroid cancer, colorectal cancer, glioma, sarcoma, glioblastoma, neuroblastoma, Wilms tumor, pancreatic cancer, head and neck cancer, cervical cancer, melanoma, breast cancer, lung cancer, mammary-analog secretory carcinoma of the salivary gland, secretory breast carcinoma, infantile fibrosarcoma, endometrial cancer, gallbladder cancer, gastrointestinal stromal tumor, mesothelioma, multiple myeloma, prostate cancer, leukemia, myeloproliferative disease, myelodysplastic syndrome, idiopathic hypereosinophilic syndrome (HES), bladder cancer, CNS cancer, esophageal cancer, liver cancer, nasopharyngeal cancer, neuroendocrine cancer, ovarian cancer, renal cancer, testicular cancer, cholangiocarcinoma, appendix tumor, and hematologic malignancy.

11. The method of claim 8, wherein the therapeutically effective amount or crenolanib or the pharmaceutically acceptable salt thereof is from about 50 to 800 mg per day, 100 to 450 mg per day, 200 to 400 mg per day, 300 to 500 mg per day, 350 to 500 mg per day, 400 to 600 mg per day, or 600 to 800 mg per day.

12. The method of claim 8, wherein the therapeutically effective amount of crenolanib or the pharmaceutically acceptable salt thereof is at least one of:
administered at least one of continuously, intermittently, systemically, or locally;
administered orally, intravenously, topically, intramuscularly, subcutaneously, or intraperitoneally;
administered up to three times or more a day for as long as the subject is in need of treatment for a proliferative disease;
administered at least one of sequentially or concomitantly, with another pharmaceutical agent in a newly diagnosed proliferative disease patient, to maintain remission, or a relapsed/refractory proliferative disease patient;
administered as a single agent or in combination with another pharmaceutical agent in a newly diagnosed proliferative disease patient, to maintain remission, or a relapsed/refractory proliferative disease patient; or
administered as a single agent or in combination with another pharmaceutical agent in a newly diagnosed proliferative disease pediatric patient, to maintain remission, or a relapsed/refractory proliferative disease pediatric patient.

13. The method of claim 8, wherein the crenolanib is a pharmaceutically acceptable salt of crenolanib.

14. The method of claim 8, wherein the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, crenolanib tosylate, crenolanib mesylate, crenolanib benzoate, or crenolanib succinate.

15. A method of inhibiting or reducing TRKC tyrosine kinase activity or expression in a subject suffering from a proliferative disorder or proliferative disease comprising:
determining that the proliferative disorder or proliferative disease exhibits one or more of overexpression, activation, amplification, or mutation of TRKC kinase; and
administering to the subject a therapeutically effective amount of crenolanib or a pharmaceutically acceptable salt thereof wherein the crenolanib or salt thereof inhibits or reduces the TRKC tyrosine kinase activity or reduces expression of the TRKC tyrosine kinase activity in a subject suffering from a proliferative disorder or proliferative disease.

16. The method of claim 15, wherein the TRKC mutation is a gene fusion; wherein the TRKC gene fusion is selected from one of AKAP13-TRKC, AML4-TRKC, ETV6-TRKC, FAT1-TRKC, LYN-TRKC, RBPMS-TRKC, TPM4-TRKC, VPS18-TRKC, KHDRBS1-TRKC, IFR2BP2-TRKC, EML4-TRKC, TGF-TRKC, or SQSTM1-TRKC; wherein the TRKC mutation is a missense, insertion, or deletion mutation; or wherein the TRKC mutation is selected from a missense mutation at least one of L686 or G696.

17. The method of claim 15, wherein the proliferative disorder or proliferative disease is selected from at least one of thyroid cancer, colorectal cancer, glioma, sarcoma, glioblastoma, neuroblastoma, Wilms tumor, pancreatic cancer, head and neck cancer, cervical cancer, melanoma, breast cancer, lung cancer, mammary-analog secretory carcinoma of the salivary gland, secretory breast carcinoma, infantile fibrosarcoma, endometrial cancer, gallbladder cancer, gastrointestinal stromal tumor, mesothelioma, multiple myeloma, prostate cancer, leukemia, myeloproliferative disease, myelodysplastic syndrome, idiopathic hypereosinophilic syndrome (HES), bladder cancer, CNS cancer, esophageal cancer, liver cancer, nasopharyngeal cancer, neuroendocrine cancer, ovarian cancer, renal cancer, testicular cancer, cholangiocarcinoma, appendix tumor, and hematologic malignancy.

18. The method of claim 15, wherein the therapeutically effective amount or crenolanib or the pharmaceutically acceptable salt thereof is from about 50 to 800 mg per day, 100 to 450 mg per day, 200 to 400 mg per day, 300 to 500 mg per day, 350 to 500 mg per day, 400 to 600 mg per day, or 600 to 800 mg per day.

19. The method of claim 15, wherein the therapeutically effective amount of crenolanib or the pharmaceutically acceptable salt thereof is at least one of:
- administered at least one of continuously, intermittently, systemically, or locally;
- administered orally, intravenously, topically, intramuscularly, subcutaneously, or intraperitoneally;
- administered up to three times or more a day for as long as the subject is in need of treatment for a proliferative disease;
- administered at least one of sequentially or concomitantly, with another pharmaceutical agent in a newly diagnosed proliferative disease patient, to maintain remission, or a relapsed/refractory proliferative disease patient;
- administered as a single agent or in combination with another pharmaceutical agent in a newly diagnosed proliferative disease patient, to maintain remission, or a relapsed/refractory proliferative disease patient; or
- administered as a single agent or in combination with another pharmaceutical agent in a newly diagnosed proliferative disease pediatric patient, to maintain remission, or a relapsed/refractory proliferative disease pediatric patient.

20. The method of claim 15, wherein the crenolanib is a pharmaceutically acceptable salt of crenolanib.

21. The method of claim 15, wherein the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, crenolanib tosylate, crenolanib mesylate, crenolanib benzoate, or crenolanib succinate.

* * * * *